United States Patent [19]

Karami

[11] 4,430,088
[45] Feb. 7, 1984

[54] DIAPER WITH CUSHIONED ELASTIC LEG HOLD EDGES

[75] Inventor: Hamzeh Karami, Tilff, Belgium

[73] Assignee: Colgate-Palmolive Company, New York, N.Y.

[21] Appl. No.: 328,296

[22] Filed: Dec. 7, 1981

[51] Int. Cl.³ .............................................. A41B 13/02
[52] U.S. Cl. ................................................... 604/385
[58] Field of Search ............................... 604/385–386, 604/388–389

[56] References Cited

U.S. PATENT DOCUMENTS

| | | | |
|---|---|---|---|
| 3,417,751 | 12/1968 | Murdoch | 604/385 |
| 3,860,003 | 1/1975 | Buell | 604/385 |
| 4,226,238 | 10/1980 | Bianco | 604/385 |
| 4,300,562 | 11/1981 | Pieniak | 604/385 |
| 4,324,245 | 4/1982 | Mesek et al. | 604/385 |
| 4,325,372 | 4/1982 | Teed | 604/385 |
| 4,337,771 | 7/1982 | Pieniak et al. | 604/385 |

*Primary Examiner*—C. Fred Rosenbaum
*Assistant Examiner*—Sherri Vinyard
*Attorney, Agent, or Firm*—Norman Blumenkopf; Herbert S. Sylvester; Murray M. Grill

[57] ABSTRACT

A disposable diaper having cushioned elasticized leg hold edges formed from elastic members secured between the backing sheet and the absorbent pad or mounted directly in the absorbent pad and adapted to overcome leakage through the leg hold edges while cushioning so as not to make indentations or marks on the infant's skin.

2 Claims, 4 Drawing Figures

DIAPER WITH CUSHIONED ELASTIC LEG HOLD EDGES

BACKGROUND OF THE INVENTION

1. Field of the Invention

This invention relates to disposable diapers and more particularly to elasticized and contoured diapers.

2. Description of the Prior Art

In the past elasticized contoured diapers have been developed such as that disclosed in the U.S. Pat. No. 3,860,003, to Buell, issued Jan. 14, 1975, for "Contractable Side Portions for Disposable Diaper" wherein elastic strips are secured to the crotch portions of the diaper and spaced at least ¾ inch from the absorbent pad to form elasticized crotch seals for securement over the legs of the infant to prevent loss of fluid from the interior of the diaper along the legs of the infant. The elasticized strips were placed more than ¾ inch from the absorbent pad in order to prevent pleats forming transversely of the crotch area of the diaper.

Another diaper is presently in production in which the elasticized strips are less than ¾ inch from the absorbent pad for the production of the transverse pleats in the crotch area of the diaper for the purpose of increasing the absorbent capacity at the crotch area of the diaper. This diaper is disclosed in U.S. Pat. No. 4,050,462. However, it has been found that these pleats may act as a channel resulting in excessive diaper leakage and the pleats in the crotch area make the infant's bottom uncomfortable when sitting, especially while the diaper is not saturated.

The elasticized construction in both the diapers as disclosed in the aforesaid patents cause marks and indents to be formed in the skin of the infant on which these types of diapers are used.

SUMMARY OF THE INVENTION

The present invention overcomes the disadvantages of both of the prior art diapers. The elastic members are placed according to the present invention within the confines of the absorbent pad or between the absorbent pad and the backing sheet cushioning the elastic action and preventing marks and indents being formed in the skin of the infant while providing unexpectedly better protection against excessive leakage through leg hold edges.

The concept of the present invention features a disposable diaper which is contoured in an hour-glass configuration and having an absorbent body between a top sheet and a backing sheet with elastic members secured between the backing sheet and the absorbent pad or disposed completely within the confines of the absorbent pad.

DETAILED DESCRIPTION OF THE INVENTION

Figure 1:
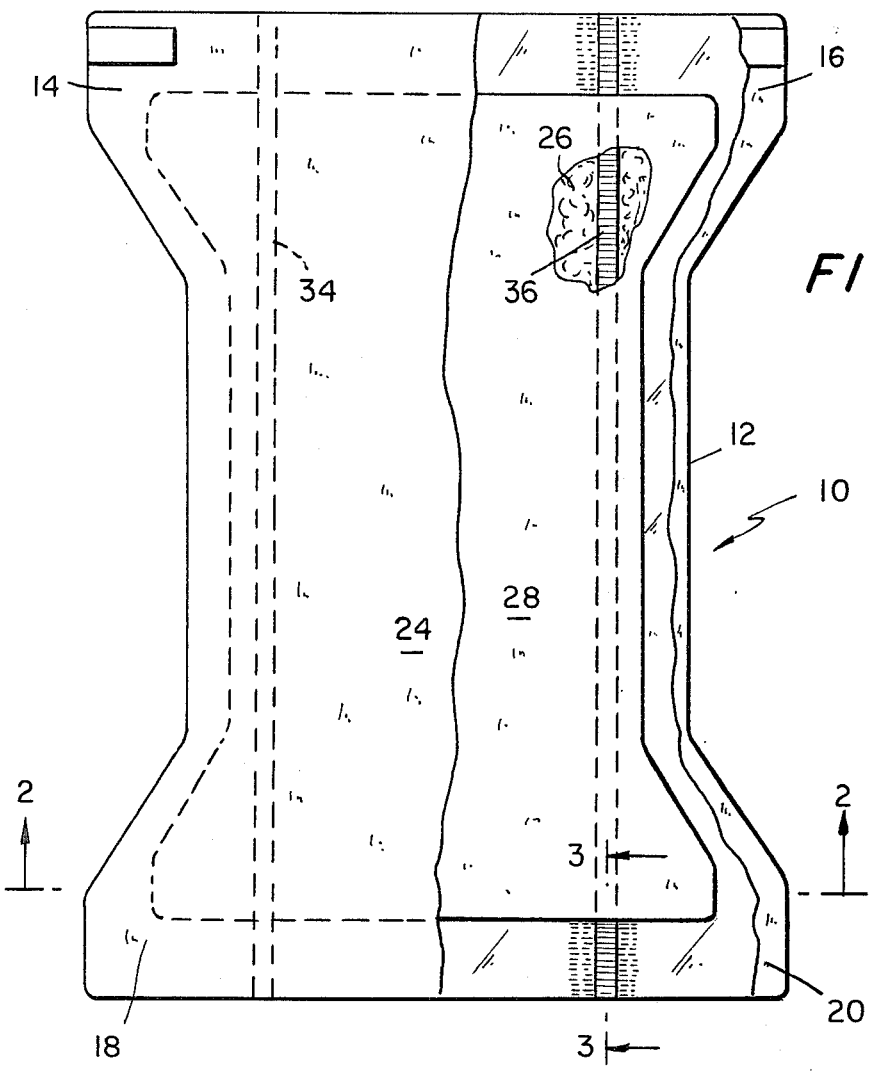
FIG. 1 is a plan view of a diaper constructed in accordance with the concepts of the present invention.

With continuing reference to the accompanying drawing, wherein like reference numerals designate similar parts throughout the various views, reference numeral 10 generally designates an elasticized and contoured disposable diaper constructed in accordance with the concepts of the present invention. The diaper is of an hour-glass configuration having a crotch area 12 and four portions of greater width defining ears 14, 16, 18, and 20. The diaper includes a backing sheet 22 of an impervious material such as polyethylene or polypropylene film. A top sheet 24, preferably of a typical nonwoven bonded (e.g. by resin latex) rayon or rayon-polyester fiber sheet or a spunbonded sheet of polyethylene or polypropylene fibers, is sealed preferably by hot melt lines to the backing sheet along the peripheral edges of the diaper. An absorbent pad 26 is disposed between the top sheet 24 and the backing sheet 22 and may be conventional wood fluff (e.g. from chemical, semi-chemical or thermo-mechanical pulp) or the like. An upper wadding sheet 28 and a lower wadding sheet 30 are provided, the pad and the wadding sheets conforming generally in contours to the hour-glass shape.

Figure 3:
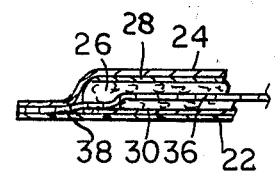
FIG. 3 is a sectional detail view taken along the plane of line 3—3 in FIG. 1; and, FIG. 4 is a partial view similar to FIG. 2, but showing a modification of the invention.
Figure 2:
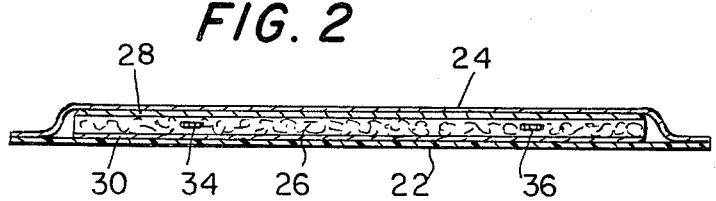
FIG. 2 is a transverse sectional view taken along the plane of line 2—2 in FIG. 1 through the crotch portion of the diaper.

A pair of elasticized strips 34 and 36 which may be provided with adhesive on at least the bottom end surfaces thereof are disposed wholly within the wood fluff of the pad 26 and may be bonded at the ends as at 38, FIG. 3, with the adhesive to the lower wadding sheet 30 or backing sheet 22 outwardly of the edges of pad 26. The adhesive may be any conventional hot melt or pressure-sensitive adhesive and, preferably, one that, at ambient temperatures is flexible and extensible (i.e. elastic-like in nature). The backing sheet 22 may have adhesive lines 25 applied there to cover which the strips 34 and 36 are mounted and adhesively secured.

The strips 34 and 36 extend the entire length of the diaper 10 and beyond the pad inwardly of the ears 12, 14, 16, 18 so that the tension provided by the elasticized strips is such that the pad 26 itself cushions the leg hold edges to form especially tight fluid seals without causing marks or idents to be formed on an infant's skin. The top and bottom wadding sheets may be conventional paper or tissue heretofore used in the art (i.e. cellulosic fibers) or may be formed of hydrophobic fibers (e.g. polyester, polyethylene or polypropylene) or rendered hydrophobic by suitable and conventional treatments (e.g. by resins).

Figure 4:
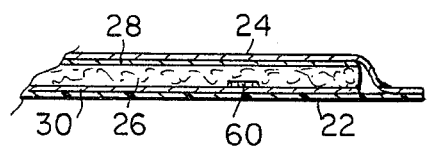

In FIG. 4 there is shown a variation wherein the entire elasticized strip 60 is bonded to either the lower wadding sheet 30, the backing sheet 22 or both below the pad 26 between the pad 26 and the backing sheet 22 so that the strips 60 cause the pad 26 to cushion the leg hold edges.

The elastic strips 34 and 36 and 60 may be varied in widths but generally from about 3 to 12 mm with a range of about strips may be somewhat greater or lesser than that of the elastic strips and typically, for a 6 mm elastic strip, would range from about 4 to 12 mm. Typical thicknesses of strips 34 and 36 range from a few mils (e.g. 1 to 5) to 15 or 20 mm. with the higher ranges more general for foams.

The elastic strips 34 and 36 may be of any suitable construction and materials such as the conventional rubberized (or otherwise elastomerized) fibers or may be simply a strip of elastomeric resin or foamed resin which may or may not be provided with adhesive. Such strips are generally available as double-sided transfer tapes (e.g. 3M Co., St. Paul. Minn., tape No. 456 high tack pressure-sensitive tape).

The top sheet 24 may be fully elasticized and provided with a waist band if desired.

What is claimed is:

1. A disposable diaper comprising a backing sheet, an absorbent pad on said backing sheet, a top sheet overlying said absorbent pad, means securing said top sheet to said backing sheet with said pad therebetween and elasticized members entirely disposed within said pad.

2. A disposable diaper according to claim 1, wherein the means securing said top sheet to said backing sheet secured the ends of said elasticized strips to said backing sheet.

* * * * *